US008764447B2

(12) United States Patent
Fieldberg

(10) Patent No.: US 8,764,447 B2
(45) Date of Patent: Jul. 1, 2014

(54) DRUG-FREE METHOD AND SYSTEM FOR REDUCTION OF LACTIC ACID WHILE TRAINING ATHLETES USING PH BALANCING

(76) Inventor: J. Harold Fieldberg, Medicine Hat (CA)

( * ) Notice: Subject to any disclaimer, the term of this patent is extended or adjusted under 35 U.S.C. 154(b) by 691 days.

(21) Appl. No.: 12/795,161

(22) Filed: Jun. 7, 2010

(65) Prior Publication Data
US 2011/0300517 A1    Dec. 8, 2011

(51) Int. Cl.
*G09B 19/00* (2006.01)
*A63B 69/00* (2006.01)

(52) U.S. Cl.
CPC ........ *G09B 19/0092* (2013.01); *G09B 19/0038* (2013.01); *A63B 69/00* (2013.01)
USPC .......................................... 434/127; 434/247

(58) Field of Classification Search
CPC . G09B 19/0038; G09B 19/0092; A63B 69/00
USPC ................................................ 434/127, 247
See application file for complete search history.

(56) References Cited

U.S. PATENT DOCUMENTS

| 4,871,550 | A | 10/1989 | Millman |
| 4,973,467 | A | 11/1990 | Sahley |
| 5,137,692 | A * | 8/1992 | Fritz .............................. 422/401 |
| 6,159,476 | A | 12/2000 | Djananov et al. |
| 6,162,472 | A * | 12/2000 | Griffin et al. ................... 426/42 |
| 6,165,105 | A | 12/2000 | Boutellier et al. |
| 6,375,956 | B1 * | 4/2002 | Hermelin et al. ............. 424/400 |
| 2001/0043925 | A1 * | 11/2001 | Hsia et al. .................. 424/93.51 |
| 2003/0031725 | A1 * | 2/2003 | Massner ....................... 424/600 |
| 2003/0180393 | A1 | 9/2003 | Stern ............................ 424/725 |
| 2008/0317936 | A1 * | 12/2008 | Magliba ....................... 426/638 |
| 2009/0068300 | A1 * | 3/2009 | Edalat .......................... 424/776 |
| 2009/0269728 | A1 | 10/2009 | Verstegen et al. |
| 2009/0297627 | A1 * | 12/2009 | Tanelian ....................... 424/643 |
| 2010/0009328 | A1 | 1/2010 | Nadeau |
| 2010/0015586 | A1 | 1/2010 | Park et al. |

\* cited by examiner

*Primary Examiner* — Xuan Thai
*Assistant Examiner* — Jerry-Daryl Fletcher
(74) *Attorney, Agent, or Firm* — RG Patent Consulting LLC; Rachel Gilboy

(57) ABSTRACT

A drug-free method for training athlete(s) using ph balancing including the steps of eating from a trainer-specified meal plan; training according to a trainer-specified training plan; and pH testing of the athlete(s). The athlete's diet is maintained according to the trainer- specified meal plan, followed by the athlete training in accordance to the trainer-specified training plan. The athlete then undergoes pH testing to determine if they have a proper body pH balance to maximize training results. Further, a kit is disclosed having a set of charts, a saliva ph tester; a urine ph tester; pre-train and post-train supplement drinks; a set of vitamin supplements; and user instructions.

1 Claim, 16 Drawing Sheets

4 Week Training Procedure — 110

Split Train 3 days per week. E.g. Monday, Wednesday, Friday

Warm up for 5-10 minutes before entering gym with cardio equipment
Stretch after workout
Very important to Execute proper form.

Week ONE Exact Program — 800
 A Use weights you can lift easily
   No Muscular failure. Let body gradually adapt to straining stress
 B Increase weights gradually each day — 102
 C Rest 2 minutes between sets

|  | Sets | Reps |
|---|---|---|
| Squats | 2 | 12 |
| Barbell Bench Press | 2 | 10 |
| Stiff-Leg Deadlift | 2 | 10 |
| Overhead Dumbbell Press | 2 | 10 |
| Standing Calf Raise | 2 | 15 |
| Bent-over Barbell Rows | 2 | 10 |
| Dips | 2 | 8-10 |
| Planks | 2 | Hold as long as you can |
| Kneeing on Ball | 2 | Hold as long as you can |

Week TWO    Exact Program Increase weights to mild stress

Week THREE Add ONE SRT to ALL exercises Add
  Weight daily to medium stress 3

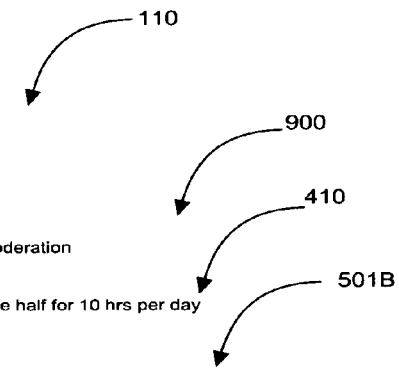

LEMON WATER PROGRAM

FRESH squeezed Yellow Lemon
Water
Total

Every hour on the hour for 10 hours per day
Example
6:00 AM 4 oz
9:00 AM 4 oz
10:00 AM 4 oz
11:00 AM 4 oz
12:00 AM 4 oz
1:00 PM 4 oz
2:00 PM 4 oz
3:00 PM 4 oz
4:00 PM 4 oz
5:00 PM 4 oz
TOTAL 40 oz OTHER FLUID
Juice, Tea Coffee. Etc. in moderation
Water preferred 40 oz Every hour on the hour on the half for 10 hrs per day Example 6:30 AM 4 oz
9:30 AM 4 oz
10:30 AM 4 oz
11:30 AM 4 oz
12:30 AM 4 oz
1:30 PM 4 oz
2:30 PM 4 oz
3:30 PM 4 oz
4:30 PM 4 oz
5:30 PM 4 oz
TOTAL 40 oz If you start at 7 am, Finish at 4 pm
If you start at 9 am, Finish at 6pm Important note for fluid intake
Body weight has to be calculated 80 kg person takes 80 oz. 80 oz 4 oz every 30 minutes for 10 hours is 80 oz total
    This is the maximum for anyone that is heavier 50 kg person takes 60 oz 60 oz 3 oz every 30 minutes for 10 hours is 60 oz total 40 kg person  40 oz 2 oz every 30 minutes for 10 hours is 40 oz total Addition al Fluids  4 oz Morning meal
(Water preferred   4 oz Noon meal
               4 oz Evening meal
               4 oz Bedtime (Any more then this goes directly to the bladder)
Replace with WATER ONLY at estimated loss(NO SODIUM OR ENERGY Replace with WATER ONLY at estimated loss
(NO SODIUM OR ENERGY SUPPLEMENTS)

WATER PREFFERENCE  1 Distilled Water
               2 Reverse osmosis water
               3 Any water IMPORTANT NOTE;; Water intake is correct when urine is clear like water

FIG. 9

FOOD CONSUMPTION

Normal Active 180 pound Adult
Adjustments shall be made for weight, Age, and Activity — 620
Grams indicated are grams digestible.
Example:

| TIME | PROTEIN | CARBOHYDRATES | FAT | OMEGA 3 |
|---|---|---|---|---|
| Grams | | | | |
| 8:00 AM | 28 | 36 | 4 | Trace |
| 10:30 AM | 7 | 9 | 1 | Trace |
| 12 Noon | 28 | 36 | 4 | Trace |
| 2:30 pm | 7 | 9 | 1 | Trace |
| 5:00 PM | 28 | 36 | 4 | Trace |
| 8:00 PM | 7 | 9 | 1 | Trace |

— 110
— 1000
— 410

PROTEIN
Anything that moves or the product of anything that moves
Exception...Soy Beans CARBOHYDRATES
L1...40% of consumption, large Cell Carbohydrates
e.g.. Broccoli, cabbage, cauliflower, lettuce, peppers
L2...40% of consumption..Concentrated
e.g. peas, carrots, corn, bread, potatoes, pasta, grains, starches
L3...20% of consumption..Fruits FAT
Source is muscle fat in low fat protein
The fat content of lean muscle protein is usually adequate Omega 3
Avocado, Almonds, Olives, Olive Oil, Fish Oil Trans Fats
All Trans Fats MUST be eliminated from the diet
ALWAYS...Check the Nutrition Label
Hydrogenated...Partially Hydrogenated
Margarine...Shortening
ARE ALL TRANS FATS

FIG. 10

CARBOHYDRATE REGULATIONS
Instrument used for testing a refactrometer
Process One drop of fresh urine on slide and viewed and recorded as BRIX
Sweetener is Added to the TOTAL Lemon Water for the day

| Energy Range | BRINX | Energy Range | Sweetener |
|---|---|---|---|
| C | 12 | 50% | NO |
| C | 8.5 | 75% | NO |
| B | 8.4 | 80% | NO |
| B | 5.5 | 90% | NO |
| B | 5.4 | 91% | 1 Tablespoon |
| B | 2.0 | 95% | 1 Tablespoon |
| A | 1.9 | 100% | 2 Tablespoon |
| A | 1.3 | 100% | 2 Tablespoon |
| D | 1.2 | 50% | 2 Tablespoon |
| D | 1.0 | 35% | 2 Tablespoon |
| D | 0.9 | 30% | 3 Tablespoon |
| D | 0.6 | 20% | 3 Tablespoon |
| E | 0.5 | 15% | 3 Tablespoon |
| E | 0.0 | 0% | 3 Tablespoon |

Sweetener to be used. Vary and Alternate with taste
  Honey....Molasses....Brown Sugar etc.

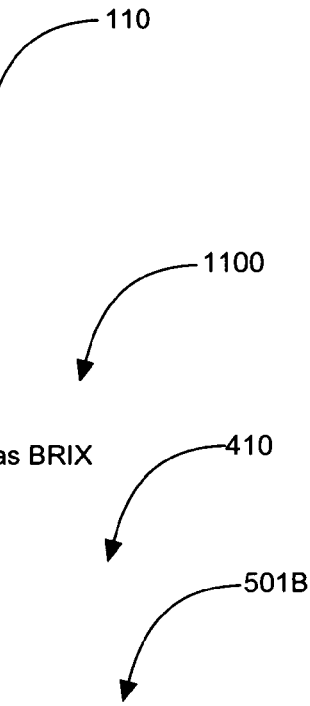

FIG. 11

Calcium Rates for Variable Ranges
Alkaline is pH 6.4 and above.
Acid is pH below 6.4
REFER TO RANGE CHART FOR RANGES

| URINE | SALIVA | AVERAGE | RANGE | CALCIUM | CAPSULES | TIMES PER DAY |
|---|---|---|---|---|---|---|
| Alkaline | Alkaline | Alkaline | AA | Calcium Lactate | 2 | 2 |
| | | | BB | Calcium Lactate | 3 | 2 |
| | | | CC | Calcium Lactate | 3 | 3 |
| | | | AB | Calcium Lactate | 2 | 2 |
| | | | AC | Calcium Lactate | 3 | 2 |
| | | | BC | Calcium Lactate | 3 | 2 |
| | | | AA | Calcium Lactate | 1 | 2 |
| Acid | Alkaline | Alkaline | AB | Calcium Carbonate | 2 | 2 |
| | | | AC | Calcium Lactate | 1 | 2 |
| | | | | Calcium Carbonate | 2 | 2 |
| | | | | Calcium Lactate | 2 | 2 |
| | | | DB | Calcium Carbonate | 1 | 2 |
| | | | DC | Same as DC | | |
| | | | | Calcium Lactate | 1 | |
| | | | EB | Calcium Carbonate | 2 | 2 |
| | | | EC | Calcium Hydroxide | 1 Tablespoon | 2 |
| | | | | Same as EC | | 2 |
| | | | | Calcium Lactate | 1 | |
| | | | | Calcium Carbonate | 3 | 2 |
| | | | | Calcium Hydroxide | 2 Tablespoon | 2 |
| | | | | Same as EC | | 2 |
| Acid | Acid | Acid | DA | Calcium Carbonate | 2 | |
| | | | EC | Calcium Hydroxide | 2 Tablespoon | 3 |
| | | | | B12-1000 mog | 1 | 2 |
| | | | DD | Tums | 2 | 1 |
| | | | ED | | | 2 |
| | | | EE | | 3 | |
| | | | | Same as CE | 2 Tablespoon | 3 |
| | | | | Same as CE | 1 | 3 |
| | | | | Same as CE | 2 | 2 |
| Alkaline | Alkaline | Alkaline | BA | Same as CE | | 3 |
| | | | BD | Same as CE | | |
| | | | BE | Calcium Carbonate | | |
| | | | CA | Calcium Lactate | 2 | 2 |
| | | | CD | B12-1000 mog | 3 | 2 |
| | | | CE | | | 2 |

FIG. 15

| VITAMIN CALCULATIONS | | | | pH | Range | Vitamin C mg | | | |
|---|---|---|---|---|---|---|---|---|---|
| ALWAYS URINE/SALIVA for Range | | | | | AVERAGE | Vitamins to Take | | | |
| | | | | pH | Range | Vitamin C | | | |
| Average is calculated by adding Urine+Saliva+Saliva | | | | | | mg | | | |
| Divide the tatal by 3 | | | | 8 | C | 4,000 | 2*per day | | |
| | | | | 7.9 | C | 4,000 | 2*per day | | |
| Example #1 | | | | 7.8 | C | 4,000 | 2*per day | | |
| Urine pH | | | | 7.7 | C | 2,000 | 2*per day | | |
| Saliva pH | | | | 7.6 | C | 2,000 | 2*per day | | |
| | | | | 7.5 | C | 2,000 | 2*per day | | |
| Urine pH | 5.8 | | | 7.4 | C | 1,000 | 2*per day | | |
| Saliva pH | 7.7 | | | 7.3 | C | 1,000 | 2*per day | | |
| Saliva pH | 7.7 | | | 7.2 | C | 1,000 | 2*per day | | |
| Total | 21.2 | | | 7.1 | B | 1,000 | 1*per day | | |
| Divide by 3 | 3 | | | 7 | B | 1,000 | 1*per day | | |
| This Equals | 7.07 | | | 6.9 | B | 1,000 | 1*per day | | |
| Closest is | 7.1 | | | 6.8 | B | 1,000 | 1*per day | | |
| pH of 7.1 has a range of B | | | | 6.7 | B | 1,000 | 1*per day | | |
| You would take vitamins in that range | | | | 6.6 | A | 500 | 2*per day | | |
| | | | | 6.5 | A | 500 | 2*per day | | |
| Example #2 | | | | 6.4 | A | 500 | 2*per day | | |
| Urine pH | 6.9 | | | 6.3 | A | 500 | 2*per day | | |
| Saliva pH | 5.6 | | | 6.2 | A | | | 1,000 | 1 each day |
| | | | | 6.1 | D | | | 1,000 | 1 each day |
| Urine pH | 6.9 | | | 6 | D | | | 1,000 | 1 each day |
| Saliva pH | 5.6 | | | 5.9 | D | | | 5,000 | 1 each day |
| Saliva pH | 5.6 | | | 5.8 | D | | | 5,000 | 1 each day |
| Total | 18.1 | | | 5.7 | D | | | 5,000 | 1 each day |
| Divide by 3 | 3 | | | 5.6 | D | | | 5,000 | 1 each day |
| This Equals | 6.03 | | | 5.5 | D | | | 5,000 | 2 each day |
| Closest is | 6 | | | 5.4 | E | | | 5,000 | 2 each day |
| | | | | 5.3 | E | | | 5,000 | 2 each day |
| | | | | 5.2 | E | | | 5,000 | 2 each day |
| | | | | 5.1 | E | | | 50,000 | 3 each day |
| | | | | 5 | E | | | 50,000 | 3 each day |
| | | | | 4.9 | E | | | 50,000 | 3 each day |
| | | | | 4.8 | E | | | 50,000 | 3 each day |

FIG. 16

DRUG-FREE METHOD AND SYSTEM FOR REDUCTION OF LACTIC ACID WHILE TRAINING ATHLETES USING PH BALANCING

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

1. Field of the Invention

The present invention relates generally to the field of training and nutrition programs and more specifically relates to comprehensive drug-free training programs for use by athletes in conjunction with ph monitoring to reduce or eliminate lactic acid.

2. Description of the Related Art

Athletes participating in various sporting events may require training programs to be competitive. Conventional physical training programs are typically executed and carried out by coaches or trainers. Athletes have different body structures and compositions which may need to be quantitatively evaluated to maximize and achieve the results from training. Custom tailoring a training program and routine to each individual's specific needs may prove difficult. If these tailor-made training programs are not suitably user-defined, an athlete cannot significantly improve. Further, when using traditional training techniques the likelihood of an athlete 'plateauing' at less than an optimum level are dramatically increased thereby resulting in lower peak energy output. This may manifest itself when an athlete is no longer able to increase their level of difficulty when exercising such as weight lifting or shorten their times when running.

Sustained exercise such as for example, marathon running increases the whole-body energy requirement by 20-30 times over resting levels. It is vital that the health of individual athletes be stable during exercise periods, competition periods, and in non-exertive durations. There are many metaphysical changes that occur within the human body during periods of intense exercise. As an example, heart rate increases, perspiration increases, internal body temperature rises, and various internal chemical reactions may take place. One of these effects is acidosis causing increases in lactate concentration during heavy exercise which may result in detrimental effects such as muscle burn.

Muscle burn is largely the result of lactic acid which indicates hydrogen ion buildup in the system. Acid concentration increases when an athlete exceeds what is called the lactate threshold, the point at which the body can no longer flush or neutralize acid wastes as fast as they are being produced. When an athlete crosses the lactate threshold for an extended time period, acid accumulates in the muscles and can lead to cramping, severely compromising athletic performance. Due to the large amounts of ATP being produced and hydrolysed in a short period of time, the buffering systems of the tissues are overcome, causing pH to fall and creating a state of acidosis, a natural process which facilitates the easier dissociation of Oxyhaemoglobin and allows easier transfer of oxygen from the blood. This may be one factor, among many, that contributes to the acute muscular discomfort experienced shortly after intense exercise. Elevated levels of lactic acid in the system are an indicator of lactic pH imbalance; hence a need exists for an athlete to be properly pH-balanced to achieve optimum results.

Balancing of pH while understanding the negative implication of pH imbalance is a vital component for elite athletes who want to reduce muscle fatigue by decreasing lactic acid which indicates hydrogen ion buildup, thereby permitting an athlete to increase performance. Obtaining a healthy pH balance may mean the difference between greater athletic accomplishments and coming up short.

Maintaining a proper pH balance is also an important aspect of maintaining a healthy lifestyle on and off the sports field. pH is measured on a 14-point scale, with 7 being deemed neutral. Pure (neutral) water has a pH around 7 at 25° C. (77° F.); this value varies with temperature. When an acid is dissolved in water the pH will be less than 7 (if at 25° C. (77° F.)) and when a base, or alkali is dissolved in water the pH will be greater than 7 (if at 25° C. (77° F.)). The lower the pH value, the higher the acidity; the higher the pH value, the more alkaline (basic). pH values vary throughout systems in the human body and should be properly balanced and maintained through diet, exercise and a healthy lifestyle.

Therefore a need exists for a comprehensive athletic training program that uses pH balancing in conjunction with individualized training, a user-defined dietary plan, with a supplement plan for each individual to obtain an optimal pH while decreasing lactic acid and hydrogen-ion build-up to achieve optimum performance.

Various attempts have been made to solve the above-mentioned problems such as those found in U.S. Pat. and Publication Nos. 6,159,476; 4,871,550; 2009/0269728; 6,165,105; 2010/0015586; 2010/0009328; and 4,973,467. This prior art is representative of training and nutrition programs. None of the above inventions and patents, taken either singly or in combination, is seen to describe the invention as claimed.

Ideally, a comprehensive athletic training program should be reliable for use with athletes of various body weights and ages and provide a safe, healthy program that can be used consistently. Thus, a need exists for a reliable comprehensive drug-free athletic training program to maximize health and training of athletes and to avoid the above-mentioned problems.

BRIEF SUMMARY OF THE INVENTION

In view of the foregoing disadvantages inherent in the known training program art, the present invention provides a novel comprehensive drug-free athletic training program and system using pH balancing. The general purpose of the present invention, which will be described subsequently in greater detail is to maximize health and training of athletes.

Disclosed herein is a drug-free method for training at least one athlete using pH balancing comprising of: eating from a trainer-specified meal plan; training according to a trainer-specified training plan; and pH testing of saliva and urine of the at least one athlete.

Using the method according to the present invention, according to the pH level, the athlete may ingest supplements; eat from the trainer-specified meal plan; train according to the trainer-specified training plan; and pH test their saliva and urine to achieve optimum training levels. The specific order may comprise: first eating from the trainer-specified meal plan; second training according to a trainer-specified training plan; third pH testing of saliva and urine of the at least one athlete; and optionally fourth ingesting supplements; fifth eating from the trainer-specified meal plan; sixth training according to the trainer-specified training plan; seventh pH testing of saliva and urine of the at least one athlete; eighth ingesting the supplements; ninth training according to the trainer-specified training plan; and tenth eating from the trainer-specified meal plan.

Additionally, a kit is embodied herein for the training system comprising: at least one set of charts; at least one saliva ph tester; at least one urine ph tester; at least one pre-train supplement drink; at least one post-train supplement drink; at least one set of vitamin supplements; and at least one set of user instructions. A refractometer may also be included to test BRIX.

The present invention holds significant improvements and serves as a drug-free method and system for training athletes using ph balancing. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, method for training athletes using ph balancing, constructed and operative according to the teachings of the present invention.

FIG. 8 illustrates an alternate exemplary training schedule that may be used in conjunction with the method of training athletes using ph balancing according to an embodiment of the present invention of FIGS. 1-5 and 7.

FIG. 9 illustrates an exemplary Lemon Water program that may be used in conjunction with the method of training athletes using ph balancing according to an embodiment of the present invention of FIGS. 1 and 4.

FIG. 10 illustrates an exemplary food consumption guide for use with the trainer-specified meal plan for the method of training athletes using ph balancing according to an embodiment of the present invention of FIGS. 1, 2, and 4-5.

FIG. 11 illustrates an exemplary carbohydrate regulation guide for use with the trainer-specified meal plan for the method of training athletes using ph balancing according to an embodiment of the present invention of FIGS. 1, 2, and 4-5.

FIG. 15 illustrates a chart showing calcium rates for variable pH ranges for use with the method of training athletes using ph balancing according to an embodiment of the present invention of FIGS. 1-3, 13, and 14.

FIG. 16 illustrates a chart showing vitamin calculations for pH values for use with the method of training athletes using ph balancing according to an embodiment of the present invention of FIGS. 1-3, 5, 6, 13-15.

The various embodiments of the present invention will hereinafter be described in conjunction with the appended drawings, wherein like designations denote like elements.

DETAILED DESCRIPTION

Figure 1:
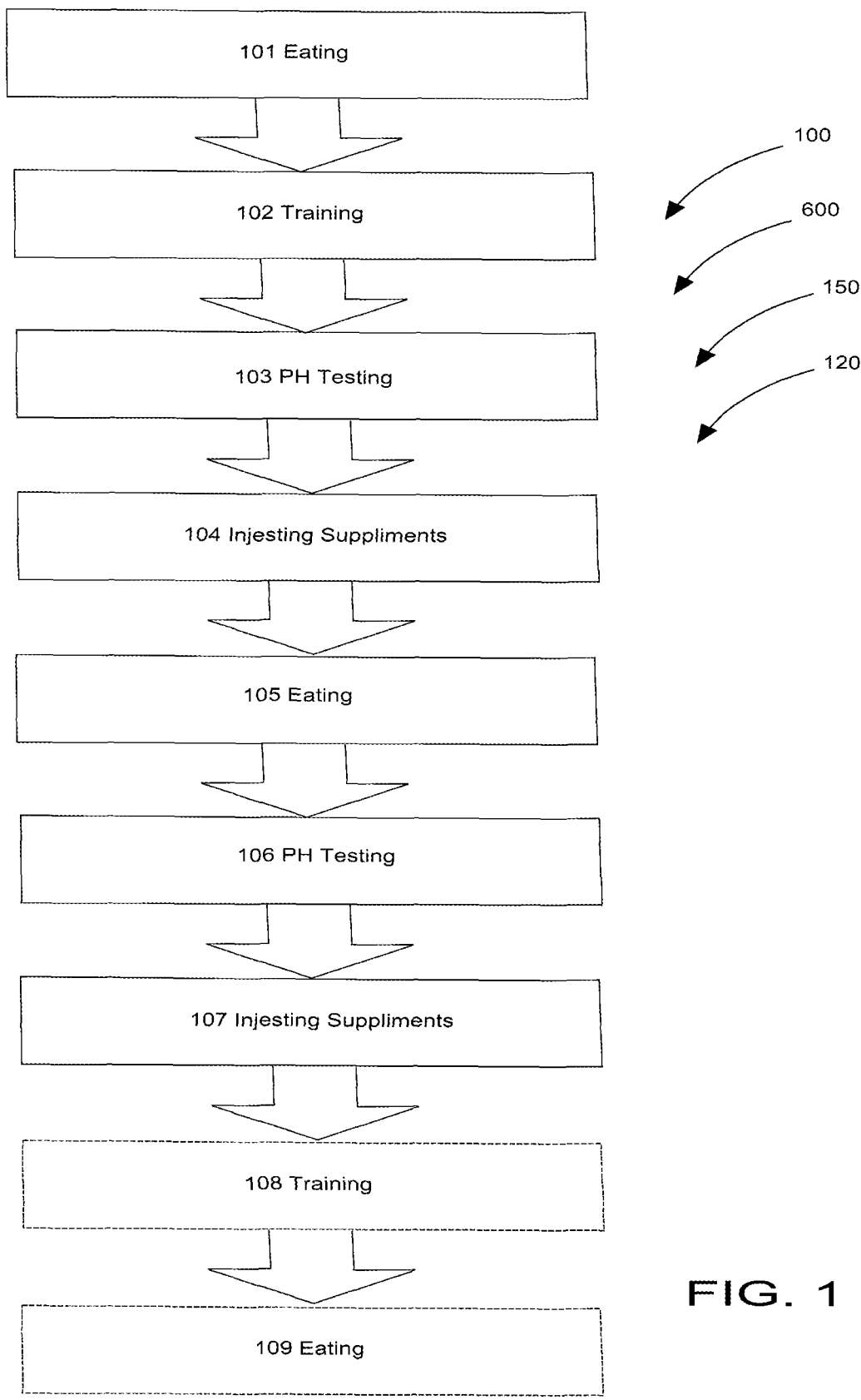
FIG. 1 shows a flowchart illustrating a method of training athletes using ph balancing according to an embodiment of the present invention.

As discussed above, embodiments of the present invention relate to a training system and more particularly to a comprehensive method and system of training athletes using ph balancing as used to improve and maximize health and training of athletes. The goal of the present inventive method is to have effectively lactic acid-free training, whereby the athlete's body does not have to handle the stress of recovery on a constant basis.

In today's society, there is a heightened interest in exercise as a way to improve the quality of one's life and physical abilities. Exercise has both acute (short-term) and chronic (long-term) effects. For the body to benefit from exercise, it is required to be able to handle both effects. When a human exercises, their systolic blood pressure, heart rate, and cardiac output all increase at a rapid pace. Blood flow to the muscles, heart, and the skin further increases. Additionally when a human is exercising, their breaths are deeper and faster to supply an adequate amount of oxygen required by the metabolism increase to remove waste products and carbon dioxide.

Elite athletes such as tri-athletes, long distance runners, body builders, swimmers, and cyclists need to find ways to manage and minimize the stress metabolically exerted onto their bodies due to strenuous and sustained routines. Additionally, these elite athletes must find ways to reduce muscle fatigue, decreasing muscle recovery time, while increasing performance. Therefore, a thorough understanding of the vital importance of pH balance and the detrimental effects of pH imbalance is key for these elite athletes to improve in their training.

Endurance and elite sport athletes preferably may be particularly concerned with maintaining a healthy pH balance, as they regularly place themselves under physical and dietary stresses that can lead to pH imbalances, most commonly lactic acid which indicates hydrogen ion buildup. A healthy pH balance may mean the difference between greater athletic achievement and being brought up short by muscle burn. Further, elite athletes should be aware about maintaining proper alkaline pH levels in the blood and tissues since the human body's entire metabolic process depends on an alkaline environment. When an athlete ingests too many acidic or acid-producing foods, excess acid corrodes tissues and organs.

According to Dr. Reams, The Reams Urine/Saliva Test measures a Person's Body Chemistry (Sugar 1.5, pH 6.4/6.4, Salt 6 to 7, Albumen 0.04M, Urea 3/3). This test yields the proper information to analyze mathematically the Body Chemistry. It makes it possible to detect, with remarkable accuracy, the locations and the severity of most physical maladies. Based on this analysis, Dr. Reams was able to prepare a specific, individualized diet designed to promote excellent health.

Dr. Reams states, "After years of testing hundreds of foods, it was found that most foods are cationic. Fresh lemons and liver bile is anionic. The minerals Calcium, Potassium, and Chlorine are also anionic. The pH is the measure of resistance between cations and anions in the Body. If the pH reading is 6.4/6.4 for urine and saliva, a person is getting maximum energy from the food that he/she is eating. If the number is either higher or lower, than is desired (over a long period of time), then too much energy is being lost, and illness may possibly occur." The inventor has found that about 70% of good health and recovery is achieved with diet and approximately 30% is conditioned upon habits and lifestyle, this using vitamins and minerals that are classified as 100% drug-free.

Therefore, dietary habits are crucial in controlling one's internal body pH levels. Dietary habits are the habitual decisions an individual or culture makes when choosing what foods to eat. However, a healthy and well-balanced diet is essential for remaining healthy and maintaining a balanced pH. Therefore acid-producing foods and beverages such as animal protein, coffee and wine should be consumed in moderation. Proper nutrition requires the proper ingestion and equally important, the absorption of vitamins, minerals, and food energy in the form of carbohydrates, proteins, and fats. Dietary habits and choices play a significant role in health and mortality. To maintain a healthy pH balance, many natural medicine practitioners recommend a diet comprised of anywhere from a 60/40 to as much as an 80/20 ratio in favor of alkalizing foods over acid-producing foods. Further, when individuals achieve pH balance through proper pH balancing, the body naturally drops to its healthy weight, muscle and joint pain will diminish and energy levels will increase immensely. Additionally, individuals having pH balanced bodies realize greater longevity, higher strengths and overall health life-quality.

The pH level is a measure of acidity or alkalinity, which takes numerical values from 0 (maximum acidity) through 7 (neutral) to 14 (maximum alkalinity). The saliva, blood, urine, digestive juices, mucus and the fluids inside and outside the body's cells each have an optimum pH level—blood pH is the most telling of all. The ideal blood pH is slightly alkaline, with a normal range of 7.35 to 7.45. If the blood pH moves below 6.8 or above 7.8, the cells of the body stop functioning and the human will die. Consequently, the body continually struggles to maintain its ideal pH.

Medical problems that may arise from unbalanced pH's are conditions such as acidosis. Acidosis is over-acidified body cells that may interrupt cellular and tissue activities and bodily functions. Possible symptoms of acidosis may include chronic muscle pain, osteoporosis, acid indigestion, joint pain, low energy, and muscle fatigue.

In addition to its various acid-flushing functions, the human body also has built-in chemical buffers that help to neutralize pH imbalances, including calcium, phosphorus, bicarbonate, hemoglobin, and phosphate cycles.

Ideally, the primary goal of the pH Diet is for athletes and non-athletes to achieve pH Balance. pH Balance is critical to achieve top athletic performance and high exercise and workout results due to the build-up of bodily acidic wastes as one exercises. Our body continually attempts to remove this acid waste and tries to neutralize the acid build-up in many ways—our kidneys filter blood and excrete acid through urine, our lungs release carbon dioxide and we also sweat acids out of our skin. Our bodies, when healthy, fit and in top shape, also have built in alkaline reserves to buffer acid and help neutralize pH imbalances.

Figure 2:
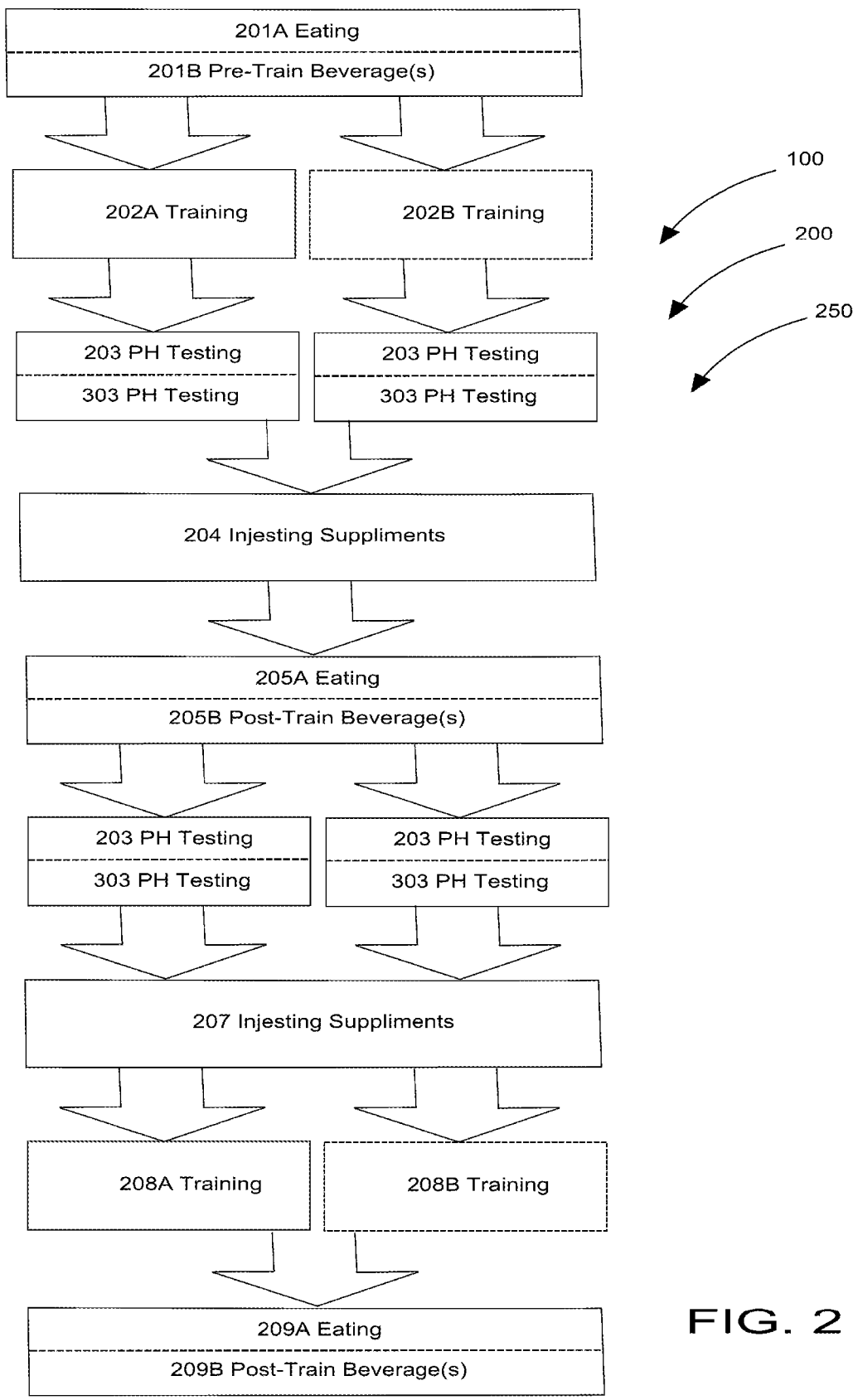
FIG. 2 is a flowchart illustrating the method of training athletes using ph balancing according to an embodiment of the present invention of FIG. 1.

Referring to the drawings by numerals of reference there is shown in FIGS. 1 and 2, flowcharts 150 and 250 respectively, illustrating method and system of training athletes using ph balancing 110 according to an embodiment of the present invention.

Figure 4:
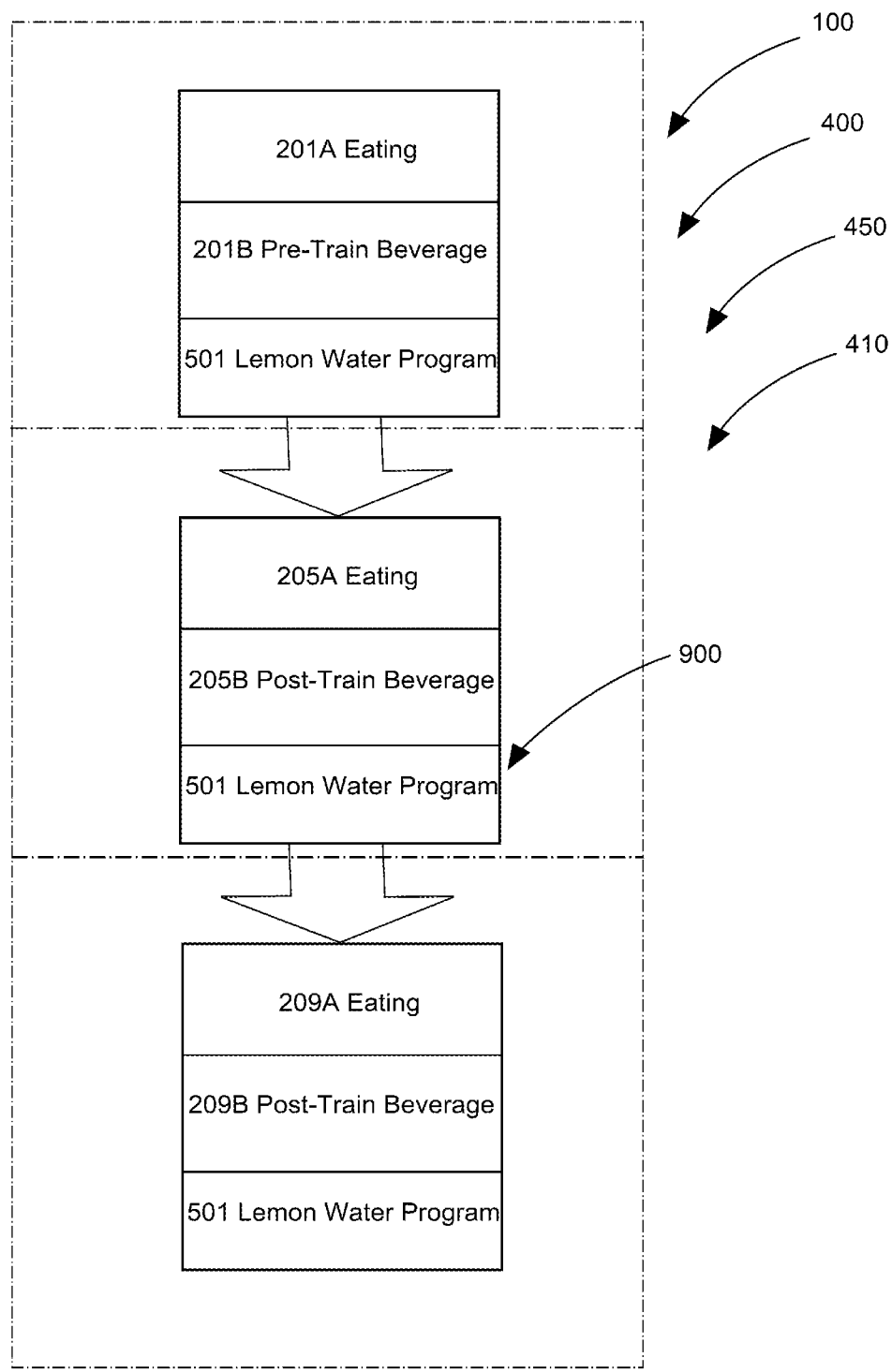
FIG. 4 is a flowchart illustrating a dietary plan used in conjunction with the method of training athletes using ph balancing according to an embodiment of the present invention of FIG. 1.

Flowchart 150 illustrates a preferred method (method and system of training athletes using ph balancing 110) for training at least one athlete using pH balancing 120 comprising the steps of: eating 101 from trainer-specified meal plan 410, also shown in FIG. 4; training 102 according to trainer-specified training plan 420; and pH testing 103 of the athlete. Preferably, the athlete eats (herein embodying eating 101) according to trainer-specified meal plan 410, followed by the athlete training 102 in accordance to trainer-specified training plan 420, and subsequently the athlete undergoes at least one pH testing 103 to determine a proper body pH balance (herein embodying pH balancing 120). In this way the present invention is used to maximize the athlete's efficiency in training 102 for competition.

Figure 3:
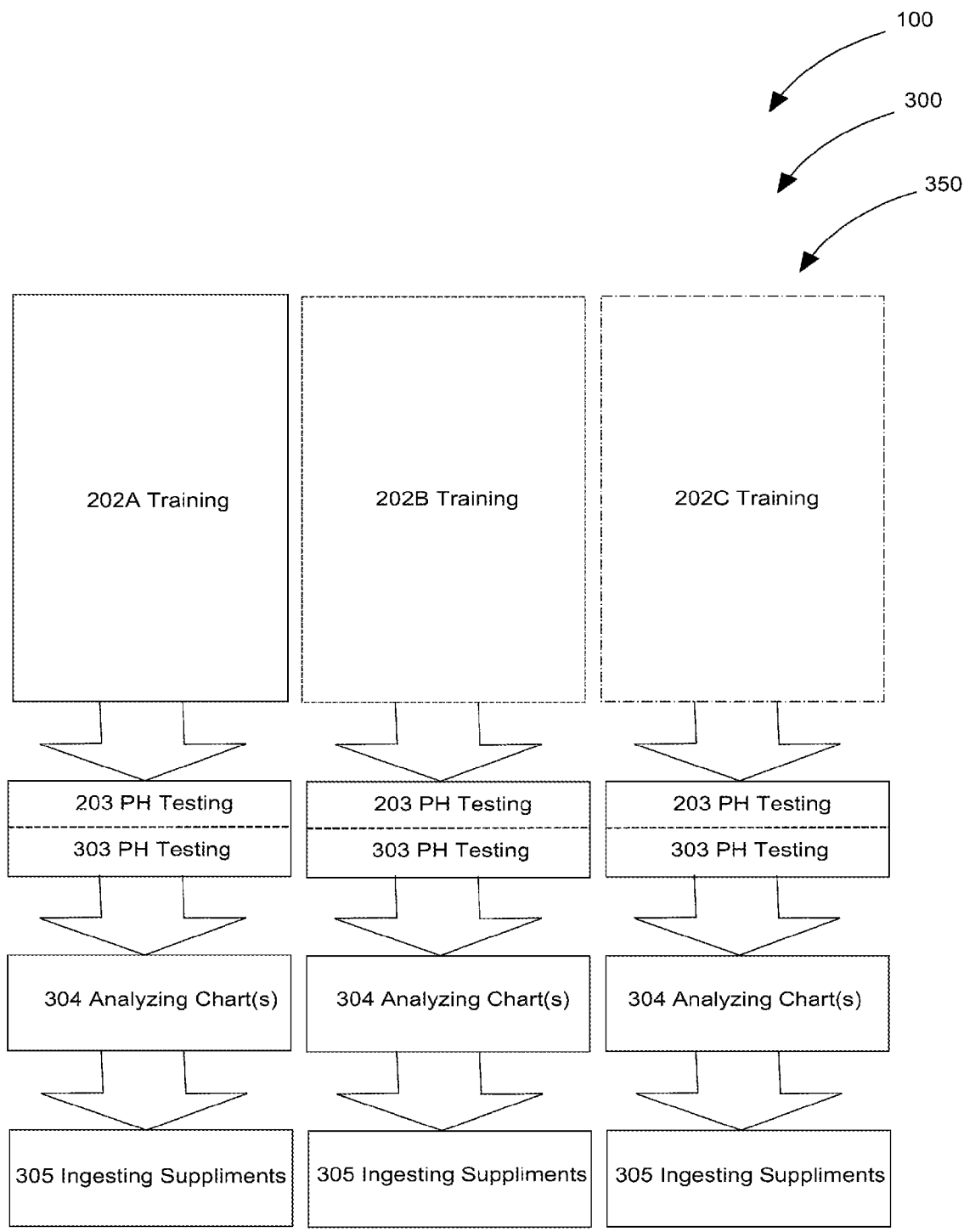
FIG. 3 is a flowchart illustrating a training plan used in conjunction with the method of training athletes using ph balancing according to an embodiment of the present invention of FIG. 1.

Flowchart 150 may also include ingesting supplements 104, discussed further in FIG. 3; eating 105 (a subsequent eating session to eating 101, as illustrated by relative ordering for example lunch); pH testing 106 (a subsequent pH testing session to pH testing 103, as illustrated by relative ordering); ingesting supplements 107 (a subsequent ingesting supplements session to ingesting supplements 104, as illustrated by relative ordering); training 108 (a subsequent training session to training 102, as illustrated by relative ordering wherein the athlete(s) train more than one session per day); and eating 109 (a subsequent eating session to eating 101, and eating 105, as illustrated by relative ordering for example dinner).

In this way the present invention may be applied to the duration of a particular time period such as over the course of a day, and may be repeated over longer or shorter durations according to the athlete's needs. Upon reading this specification, it should be appreciated that, under appropriate circumstances, considering such issues as user/trainer/athlete's preferences, time and fitness requirements, health requirements, marketing preferences, cost, available schedules, technological advances, etc., other training, eating, pH testing, ingesting of supplements in various time durations or arrangements such as, for example, part days, weeks, months, years, etc., may be sufficient. Ideally, a trainer will work in conjunction with the athlete to plan and execute the above-mentioned method and system of training athletes using ph balancing 110.

Referring now to FIG. 2 illustrating a more detailed flowchart 250 of method and system of training athletes using ph balancing 110 consisting of the ordered steps of: eating 201A (eating 101 from FIG. 1) from trainer-specified meal plan 410; training 102 (shown as training 202A and training 202B, respectively embodying different training regimens as also illustrated in FIG. 3) according to a trainer-specified training plan 420; and pH testing 203 and 303, respectively of the saliva and urine of the athlete; followed by ingesting supplements 204, as per trainer and/or doctor recommendation; eating 205A (eating 105 in FIG. 1) and consuming post-train supplement drink 205B from trainer-specified meal plan 410. It should be appreciated that in other forms/methods of the present invention, the next step may comprise an optional training session (not shown) according to trainer-specified training plan 420. Supplements 204 preferably comprise Calcium lactate, Calcium Carbonate, Calcium Hydroxide, Calcium Glucanate, and Vitamin C and Vitamin D. Those with ordinary skill in the art will now appreciate that upon reading this specification and by their understanding the art of athletic training and fitness as described herein, methods of requiring various customized athlete and sport-specific exercising regimens at different intervals will be understood by those knowledgeable in such art. It is presumed that the relative health of athlete will be monitored during the entire process.

Next in flowchart 250 is illustrated pH testing 203 and 303 of saliva and urine of the athlete(s); followed by ingesting supplements 207 such as Calcium Lactate and other calciums (as described above and according to charts provided in kit 640) to achieve pH balancing 120; training 208A or training 208B according to trainer-specified training plan 420; and preferably eating 209A and post-train supplement drink 209B from trainer-specified meal plan 410. It should be noted that pH testing 203 and 303 of saliva and urine of the athlete may be done both before and after training 208A or training 208B.

The specific order must consist of: first eating 201A from trainer-specified meal plan 410; second pH testing 203 and 303 of saliva and urine of the athlete; third training using training 202A and training 202B according to a trainer-specified training plan 420; fourth pH testing 203 and 303 of saliva and urine of the athlete; fifth ingesting supplements 204; sixth eating 205A from trainer-specified meal plan 410; seventh optionally training 102 according to trainer-specified training plan 420; and eighth pH testing 203 and/or 303 of (saliva and urine pH testing) of at least one athlete; ninth ingesting supplements 207; tenth training 208A and/or 208B according to trainer-specified training plan 420; and eleventh eating 209A from trainer-specified meal plan 410.

It should be noted that optional steps and may not be implemented in all cases. Optional steps of method and system of training athletes using ph balancing 110 are illustrated using dotted lines in FIGS. 1-5 so as to distinguish them from the other steps in flowcharts 150, 250, 350, 450, and 550.

It should be noted that the steps described in method and system of training athletes using ph balancing 110 can be carried out in many different orders according to user preference. Upon reading this specification, it should be appreciated that, under appropriate circumstances, considering such issues as design preference, user preferences, marketing preferences, cost, structural requirements, available materials, technological advances, etc., other methods of use and arrangements such as, for example, different orders within above-mentioned list, elimination or addition of certain steps, including or excluding certain training or dietary/medical steps, etc., may be sufficient.

Figure 7:
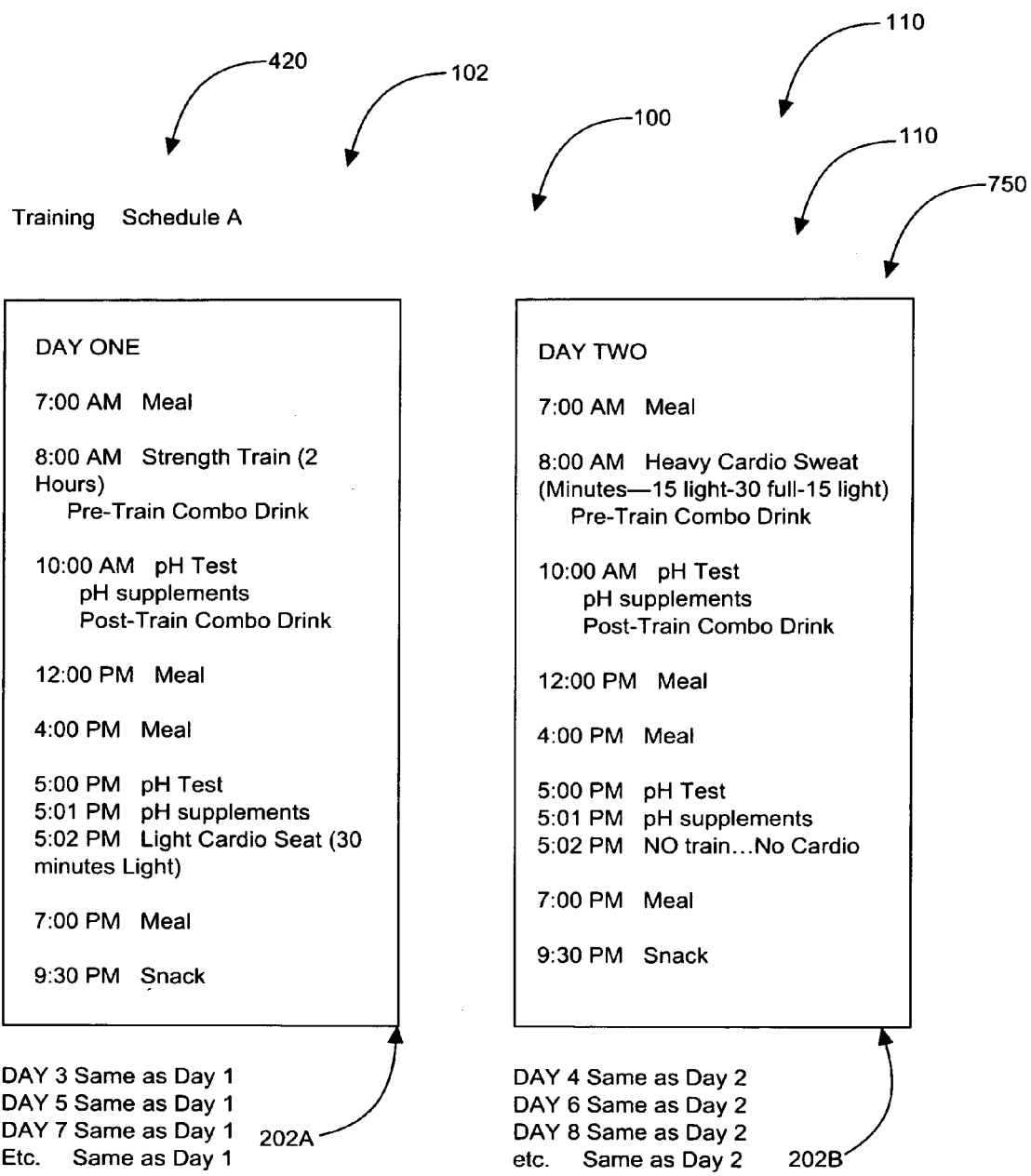
FIG. 7 illustrates an exemplary training schedule that may be used in conjunction with the method of training athletes using ph balancing according to an embodiment of the present invention of FIGS. 1-4 and 5.

Referring now to FIGS. 3 and 7, FIG. 3 showing a flowchart 350 illustrating training system 100 as used in conjunction with the method of training athletes using ph balancing 110 and FIG. 7 illustrating an exemplary training schedule 750 that may be used in conjunction with the method of training athletes using ph balancing 110 according to an embodiment of the present invention of FIGS. 1-4 and 5.

As previously discussed in FIGS. 1 and 2, training 102 may comprise different regimens and are illustrated as training 202A; training 202B; and training 202C. Training 202A; training 202B; and training 202C may comprise many different versions some exemplary sessions may include those as shown in FIG. 7 for illustration purposes. It should be appreciated that according to age, fitness, sport, activity and health of athlete that such training may differ according to need and that other regimens should be considered within the scope of the present invention. It should also be noted that training 202A; training 202B; and training 202C may comprise rest and non-rest periods. Further, drug-free within the scope of this application is with respect to the World Anti-Doping Agency Code (WADA and other such sporting agency codes) and does not refer to prescription drugs taken upon a doctor's referral. It should be noted that no anabolic steroids, growth hormones, blood doping or masking agents are used, meeting the requirements for professional athletes associations from all sports in a drug-free manner.

For example training 202A may include 7:00 AM eating 101; at 8:00 AM taking pre-train supplement drink 201B and strength version of training 102 for a period of approximately two hours (greater than, less than or equal to) followed by drinking at least one post-train supplement drink 205B at 10:00 AM after pH testing 203 and 303 (of saliva and urine) and accordingly ingesting supplements 305 according to charts (herein embodying analyzing charts 304). At 12:00 PM the athlete may commence eating 205A; and again at 4:00 PM eating 205A; followed at 5:00 PM with pH testing 203 and 303 (of saliva and urine) and at 5:01 PM ingesting supplements 305 such as Gelatin; Whey protein or other such protein source; Dry Vitamin E; Calciums (as shown in FIG. 15) and other necessary supplements that bring pH balancing 120 to an ideal range as specified subsequently herein.

At 5:02 PM athlete may do a light version of training 102 such as a light cardio sweat for about 30 minutes. At 7:00 PM athlete may eat (eating 209A) and have a light snack at 9:30 to complete a regimen for that particular day. The athlete may follow this regimen on for example Monday (day 1), Wednesday (day 3), Friday (day 5), and optionally Sunday (day 7) or alternately have Sunday as a resting period. This particular regimen may be exchanged for another or alternated with other regimens and be done on different days, however this has been provided in FIG. 7 as an exemplary means whereby another user may duplicate the results and use training system 100 of method and system of training athletes using ph balancing 110. Training 202A in this version emphasizes strength training and comprises a smaller element cardio exercise. It should be noted that preferably lemon water 501B, or alternately pure water be taken as directed to flush the toxins from the system of the athlete in all of training 202A, 202B, and 202C, as shown and discussed in FIG. 4. It should be appreciated that the present inventive method is designed to provide the athlete with the maximum physical and mental conditioning via proper nutrition, being lactic-acid free and at an optimum pH balance, as described herein.

Additionally, the recovery time is greatly decreased after sporting events and/or bodily injuries.

Within a preferred version of method and system of training athletes using ph balancing 110 training 202B may include 7:00 AM eating 101; at 8:00 AM taking pre-train supplement drink 201B and heavy cardio (about 15 minutes light cardio sweat, followed by 30 minutes of heavy sweat training, next another 15 minutes of light cardio sweat as a cool-down period) of training 102 for a period of greater than, less than or equal to aforementioned times followed by drinking at least one post-train supplement drink 205B at 10:00 AM after pH testing 203 and 303 (of saliva and urine) and accordingly ingesting supplements 305 according to charts (herein embodying analyzing charts 304). At 12:00 PM the athlete may commence eating 205A; and again at 4:00 PM eating 205A; followed at 5:00 PM with pH testing 203 and 303 (of saliva and urine) and at 5:01 PM ingesting supplements 305.

At 5:02 PM athlete may do no training 102 in this version. At 7:00 PM athlete may eat (eating 209A) and have a light snack at 9:30 to complete a regimen for that particular day. The athlete may follow this regimen on for example Tuesday (day 2), Thursday (day 4), Saturday (day 6), and optionally on to (day 8) or alternately day 8 may serve as a resting period. This particular regimen may be exchanged for another or alternated with other regimens and be done on different days, however this has been provided in FIG. 7 as an exemplary means whereby another user may duplicate the results and use training system 100 of method and system of training athletes using ph balancing 110. Training 202B in this version emphasizes cardio exercise and comprises a smaller element of strength training, thus creating a well-rounded workout regimen. Training 202C may comprise resting or alternately another regimen.

Referring specifically back to FIG. 3, within the preferred embodiment of method and system of training athletes using ph balancing 110 supplements are ingested to adjust to proper body pH balance, (hereby embodying pH balancing 120). Proper body pH balance is optimized within the preferred embodiment at 6.4 on a pH scale, specifically because athlete's body when in the range of 6.4 produces no lactic acid when training 102. The inventor has discovered through research of his own, that of Dr. Reams, from The Plant World and others that plants with an exact pH of 6.44 are effectively immune from attacks by insects because of its inherent vibrant health at that particular pH level. Dr. Reams suggests that a range of 6.2 to 6.6 is good, the Plant World suggesting that 6.44 optimum. In the same way equating to human health, humans operate most efficiently with the proper pH balancing 120. At this level athletes may realize that critical edge whereby their bodies perform at maximum, yet healthy efficiency sufficient to provide winning results.

Method and system of training athletes using ph balancing 110, as described includes pH testing 203, taken from at least one saliva sample from the athlete using pH litmus paper that is readily available at most health stores or swimming pool supply stores. In this way the present invention is cost-effective and accessible to its users. The litmus paper gives adequate results for testing used in conjunction with the provided color charts.

Additionally, pH testing 303 is taken from at least one urine sample from the athlete. Preferably, pH testing 203 is taken from at least one saliva sample and pH testing 303 is taken from at least one urine sample and are compared to a pH to Range conversion chart 1300 (of charts 610) to determine actual body pH balances, thereby pH balancing 120. Ideally the athlete shows a pH of 6.44. The closer to this range, the more efficient and healthy the body will perform, especially given stress conditions such as exercise because lactic acid is effectively eliminated.

Figure 13:
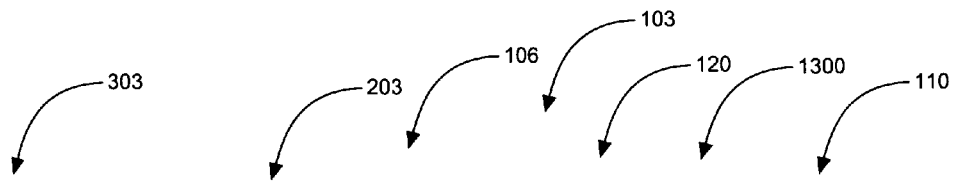
FIG. 13 is a pH to Range conversion chart for use with the method of training athletes using ph balancing according to an embodiment of the present invention of FIGS. 1-3 and 5.
Figure 14:
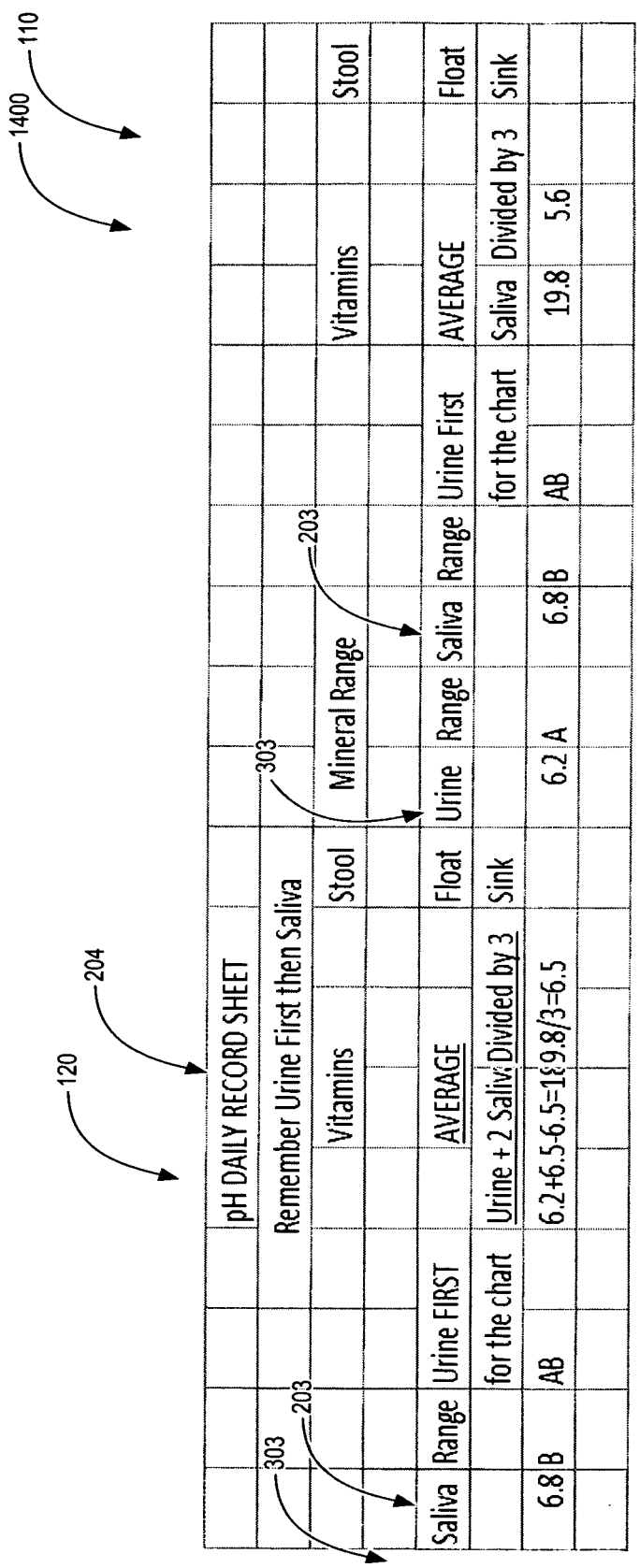
FIG. 14 illustrates an exemplary daily pH recording chart for use with the method of training athletes using ph balancing according to an embodiment of the present invention of FIGS. 1-3, 5 and 13

The preferred method for testing and recording pH testing 203 and pH testing 303 (saliva and urine respectively) is as follows: 1) Testing pH of the urine (hereby embodying pH testing 303) is done preferably by step one placing a drop of urine on the slide of the pH tester; step two recording the number displayed in the 'Urine' column on the pH Daily Recording Sheet (FIG. 14), step three locating the "Urine pH number" (pH testing 303) on the pH Range Conversion Chart (FIG. 13); and step four recording the adjacent letter found in the Urine Range column on the pH Daily Record Sheet (FIG. 14). Finally the slide should be rinsed in clear water and gently dried.

Testing the pH of saliva (pH testing 203) preferably comprises the following steps: step one place a drop of saliva on the slide of the pH tester; next step two record the number displayed in the column "Saliva" on the pH Daily Record Sheet (FIG. 14); step three comprises locating the Saliva pH number (hereby embodying pH testing 203) on the pH Range Conversion Chart (FIG. 13); and step four recording the adjacent letter found in the Saliva Range column on the pH Daily Record Sheet (FIG. 14). Record both letters in the Urine First for the Chart column on the pH Daily Record Sheet (FIG. 14). Finally the slide should be rinsed in clear water and gently dried. It should be noted that a pH tester is required for the test disclosed above, such as described previously in this document.

A refractometer may also be used to check Brix via a visual readout, the sugar and salt levels in the athlete's body as described below. The preferred procedure for recording the Brix number of the urine is as follows: step one placing a drop of urine on the slide of the refractometer; step two recording the number displayed on the slide in the 'Brix" column on the pH Daily Record Sheet (FIG. 14). In this way analyzing charts 304 using charts 610 are enabled for use with each other to obtain maximum benefit from the present invention, method and system of training athletes using ph balancing 110.

Brix is typically used in the food industry for measuring the approximate amount of sugars in fruits, vegetables, juices, wine, soft-drinks and in the starch and sugar manufacturing industry. Different countries use the scales in different industries; in the UK brewing is measured with specific gravity X 1000, European brewers use Plato degrees, and US industries use a mix of specific gravity, Brix, degrees Baumé and Plato degrees. For fruit juices, one degree Brix is about 1-2% sugar by weight. This usually correlates well with perceived sweetness.

Degrees Brix is a measurement of the fraction of sugar per hundred parts aqueous solution, by mass. It is measured with a saccharimeter, an instrument that measures specific gravity of the liquid, or more easily with a refractometer. The present invention makes use of a refractometer because it is user-friendly and cost-effective in use. For example, a 25° Bx solution is 25% sugar, or 1 part sugar to 3 parts water.

When a refractometer is used, it is correct to report the result as "refractometric dried substance" (RDS). A liquid may be referred to as being 20° Bx RDS, for example. This is a measure of percent weight of total dried solids and, although not technically the same as Brix degrees determined through a specific gravity method, renders an accurate measurement of sucrose content since the majority of dried solids are in fact sucrose. When an infrared Brix sensor is used, it measures the vibrational frequency of the sugar molecules, giving a Brix degrees measurement. This will not be the same measurement as Brix degrees using a density measurement because it will specifically measure dissolved sugar concentration instead of all dissolved solids. The index of refraction and density of mixtures such as ethanol and water are calculated using the Gladstone-Dale relation. FIG. 11 shows Brix in regulating carbohydrates in trainer-specified meal plan 410.

Figure 5:
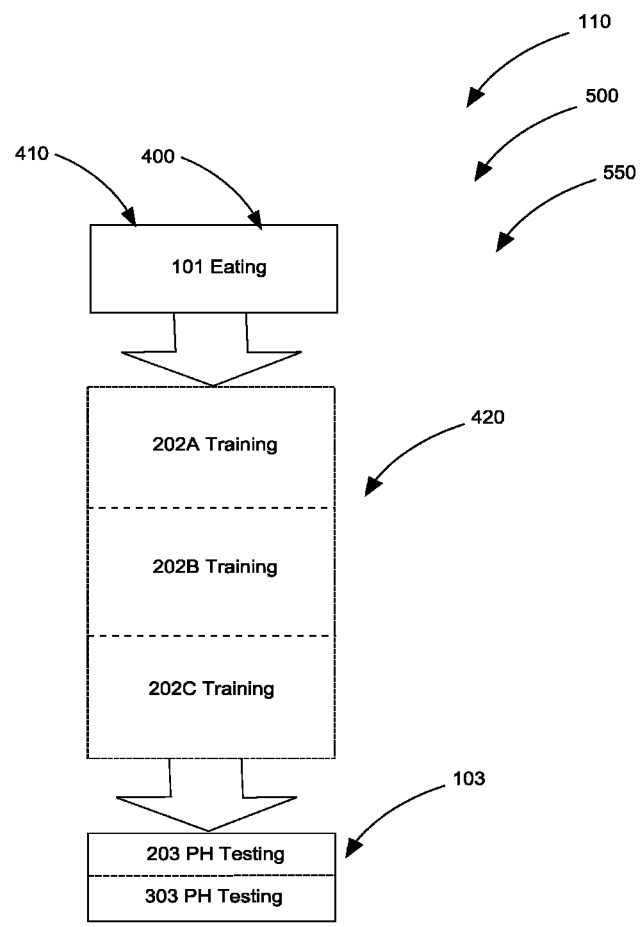
FIG. 5 is a flowchart illustrating a combination of the training and dietary plans used in conjunction with the method of training athletes using ph balancing according to an embodiment of the present invention of FIGS. 1-4.

Referring now to FIGS. 4 and 5, FIG. 4 showing flowchart 450 illustrating dietary plan 400 used in conjunction with method of training athletes using ph balancing 110 according to an embodiment of the present invention of FIG. 1.

FIG. 5 is a flowchart 500 illustrating a combination of training system 100 and dietary plan 400 used in conjunction with method of training athletes using ph balancing 110 according to an embodiment of the present invention of FIGS. 1-4.

The success of the present inventive method unequivocally depends on the dedication to following strictly trainer-specified meal plan 410, trainer-specified training plan 420, using pH balancing 120 as described herein. Trainer-specified meal plan 410 comprises lemon water 501B (the lemon water program as described by Dr. Reams) to be used as a dieretic. Trainer-specified meal plan 410 works to its optimum following the general guidelines: 1) drinking lemon water 501B; 2) eliminating transfats; 3) balancing the carbohydrates and proteins as described in charts 610; 4) taking Omega 3; 5) eliminating caffeine and any diet or sugar free products, or sugar substitutes; and 6) eliminating pork. The last item, eliminating pork, is not crucial but it may fine-tune the athlete when he/she gets to the stage of striving for the final 'edge'. This is because the frequency of pork is too close to that of humans and it digests rapidly creating poor digestion. As shown in the corresponding figures, dietary plan 400 comprises normal (everyday) foods in the proper amounts for each of the nutrients required. In this way dietary plan 400 is safe and cost-effective. Supplements in a similar manner are safe and cost-effective and available at local supermarkets.

Omega 3 fat acids within the present invention include Avocado, almonds, olives, olive oil and fish oil. n−3 fatty acids are a family of unsaturated fatty acids that have in common a final carbon-carbon double bond in the n−3 position; that is, the third bond from the methyl end of the fatty acid. Nutritionally important n−3 fatty acids include a-linolenic acid (ALA), eicosapentaenoic acid (EPA), and docosahexaenoic acid (DHA), all of which are polyunsaturated. The human body cannot synthesize n−3 fatty acids de novo, but it can form "long chain" 20-carbon unsaturated n−3 fatty acids (like EPA) and 22-carbon unsaturated n−3 fatty acids from the 'short chain' eighteen-carbon n−3 fatty acid α-linolenic acid. The short chain n−3 fatty acids are converted to 'long chain' forms with an efficiency of approximately 5% in men, and at a greater percentage in women.

When the athlete's body is in the range of 6.4, then there is effectively no lactic acid when training, thereby eliminating much of the burning pain, 'the wall'. Trainer-specified meal plan 410 comprises at least one pre-train combo drink comprising about 8 oz. volume having the minerals needed for the pH balancing 120. The minerals, supplements may comprise Folic Acid; Vitamin D; standard calciums. This allows for when the pH test 103 (203 or 303) is done pH balancing 120 can be fine tuned. Gelatin; Whey protein; Dry Vitamin E and others may be included to supplement the pH and nutritional needs of the athlete(s).

Trainer-specified meal plan 410 comprises at least one post-train supplement drink 209B which may comprise similar ingredients to pre-train supplement drink 201B, however different in the aspect that they meet the needs of the depletion of minerals during the work-out as versus what is needed for energy going into work-out session. Pre-train supplement drink 201B and post-train supplement drink 209B may be tailor-made to fit the individual needs/requirements of the athlete.

A carbohydrate is an organic compound with the general formula $Cm(H2O)n$, that is, consists only of carbon, hydrogen and oxygen, the last two in the 2:1 atom ratio. Carbohydrates can be viewed as hydrates of carbon. Carbohydrates are important within trainer-specified meal plan 410 because as directed they serve to promote the storage of energy, are an important component of DNA, play a key roles in the immune system, fertilization, pathogenesis, blood clotting, and development within the athlete's body and systems. Further, proteins and fat are necessary building components for body tissue and cells, and are also a source of energy for the athlete using dietary plan 400.

For method and system of training athletes using ph balancing 110 to work properly dietary plan 400 must be strictly adhered to; pH testings 103, and 106 and recordings must be taken and recorded upon rising, before and after each session of training (102 and 108), and 2 hours prior to bed or as required according to trainer; training 102 and 108 preferably comprising 2 training sessions of 2 hours each per day for 6 days a week, minimum program is 20 weeks, and extended program depending on requirements of specific athlete(s); recovery program (not shown) comprising of 1 hour of recovery after each of training 102 and 108 for ingesting supplements 107, timing of recovery comprising continuous from one training 102 to training 108, monitoring results; and recuperation time varying as to the occupation and requirements of the subject athlete/individual.

Recovery and recuperation time is dramatically reduced over a 20 week program realizing approximately 50-80% decrease in recovery time, very important for use with such sports as football, hockey, boxing, baseball, basketball, weight-lifting and other such sporting activities. Recovery and recuperation time may also be affected by Brix reading and salt content of the initial physical body of the individual athlete. A conditioned athlete with a healthy body may experience 80% shorter recovery time than a conditioned athlete in a poor state of health, however all athletic bodies may be shown to realize 50% shorter recovery times. It should be appreciated that the athlete must be committed to the program and to the 'lifestyle' for it to be successful.

Figure 6:
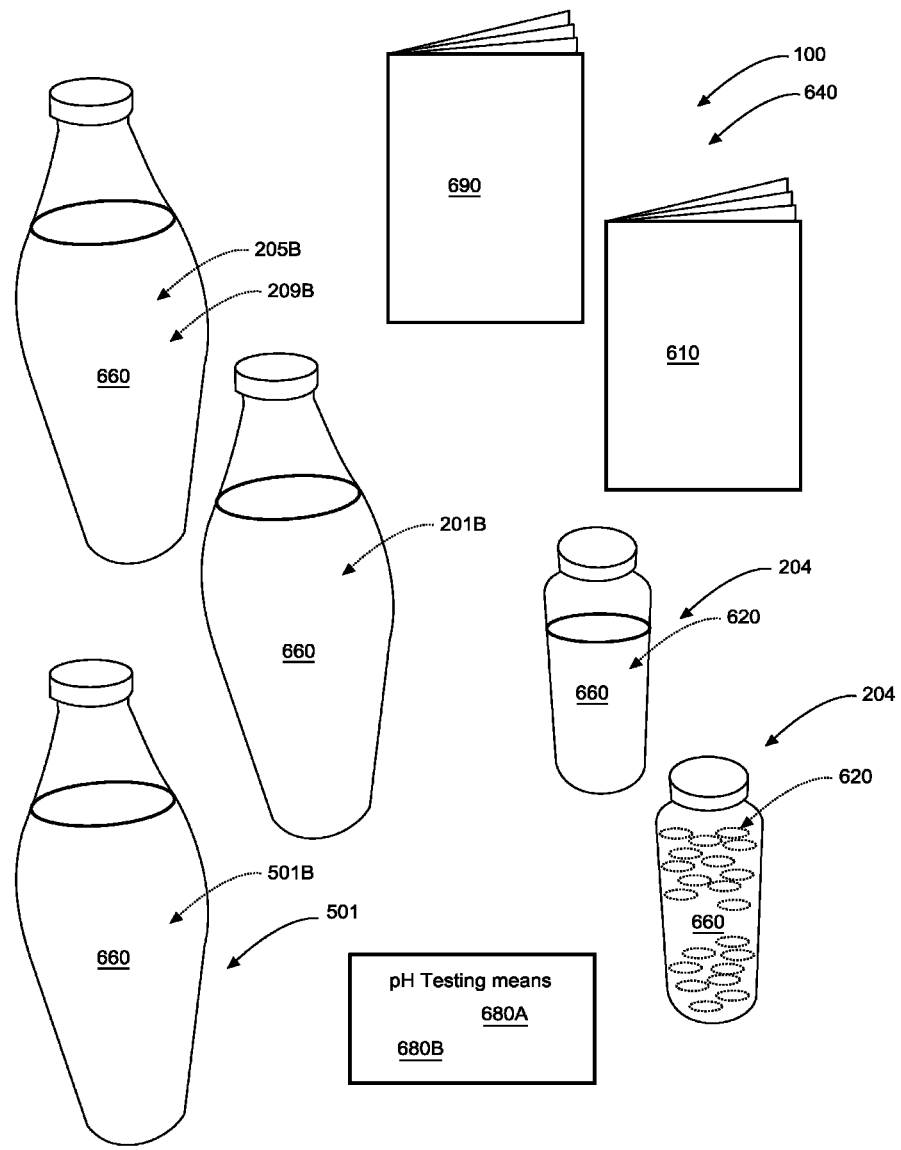
FIG. 6 is a perspective view illustrating a kit for use with the method of training athletes using ph balancing according to an embodiment of the present invention of FIGS. 1-5.

FIG. 6 is a perspective view illustrating kit 640 for use with method of training athletes using ph balancing 110 according to an embodiment of the present invention of FIGS. 1-5.

Training system 100 may be sold as kit 640 comprising the following parts: at least one set of charts 610 at least one saliva ph tester 680A; at least one urine ph tester 680B; at least one pre-train supplement drink 201B; at least one post-train supplement drink 205B or 209B (as shown); optionally lemon water 501B, (contained in various profile container(s) 660) at least one set of vitamin supplements 620; and at least one set of user instructions 690. Vitamin supplements 620 may be in liquid or granular form (powder) within the present embodiment (as alluded to in the present figure). Optionally a refractometer may be included (not shown) for testing BRIX, the sugar and salts and provides the user with a visible readout. The BRIX is an indicator means of the sugar and salt levels in the body. Training system 100 may be manufactured and provided for sale for a wide variety of athletes and non-athletes with different weights, body structures, and ages, etc. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different drink or granular combinations, charts may be sold separately, etc., may be sufficient.

FIG. 7 is discussed primarily in conjunction with FIG. 3. Referring now to FIGS. 8-16, FIG. 8 illustrating an alternate exemplary training schedule 800 that may be used in conjunction with method of training athletes using ph balancing 110 according to an embodiment of the present invention of FIGS. 1-5 and 7. Alternate exemplary training schedule 800, as shown may be used as training 102, shown in FIG. 1 or as training 202A, training 202B, training 202C, training 208A, and/or training 208B. Alternate exemplary training schedule 800 is suitable for use with athletes requiring strength training. As discussed, other forms of alternate exemplary training schedule 800 may be used with other exercises, using different repetitions, different sets, in different orders, etc.

FIG. 9 illustrates an exemplary Lemon Water Program 900 (herein embodying lemon water 501B) that may be used in conjunction with method and system of training athletes using ph balancing 110 according to an embodiment of the present invention of FIGS. 1 and 4. FIG. 9 has been provided from Dr. Reams and incorporated into the present method to enhance trainer-specified meal plan 410 by effectively flushing the athlete's system to rid the body of toxins. Lemon Water Program 900 provides directions and ingredients for making lemon water 501B. Also provided are doses to be taken at suggested intervals over at least one duration such as a portion of a day. Additionally, the calculations as per body weight of the athlete are included for ease of use. Lemon Water Program 900 provides a means whereby a user-athlete is suitable replenished with bodily fluids and hydrated to maintain a healthy metabolism.

FIG. 10 illustrates an exemplary food consumption guide 1000 for use with trainer-specified meal plan 410 for method and system of training athletes using ph balancing 110 according to an embodiment of the present invention of FIGS. 1, 2, and 4-5. Exemplary food consumption guide 1000 is based on a typical 180 lb adult and adjustments may be made for weight, age and activity, as shown. Times are provided for intake of protein, carbohydrates, fat and Omega 3 portions. Exemplary food consumption guide 1000 also discusses preferred sources for the protein, carbohydrates, fat and Omega 3. It is crucial to use Lemon Water Program 900 in conjunction to flush user's system to maintain maximized health as discussed in FIG. 9.

FIG. 11 illustrates an exemplary carbohydrate regulation guide 1100 for use with the trainer-specified meal plan 410 for method and system of training athletes using ph balancing 110 according to an embodiment of the present invention of FIGS. 1, 2, and 4-5. Exemplary carbohydrate regulation guide 1100 also discloses using a refractometer, as discussed also in FIG. 3, to obtain a Brix number. As shown readings of 1.9 and 1.3 are optimum, giving an energy range of "A" (in the Energy Range column). It is preferred that the athlete will realize maximum energy output potential. The corresponding sweetener is shown to be added to the total lemon water 501B for the day. Sweeteners such as honey, molasses and brown sugar may be used as specified.

Figure 12:
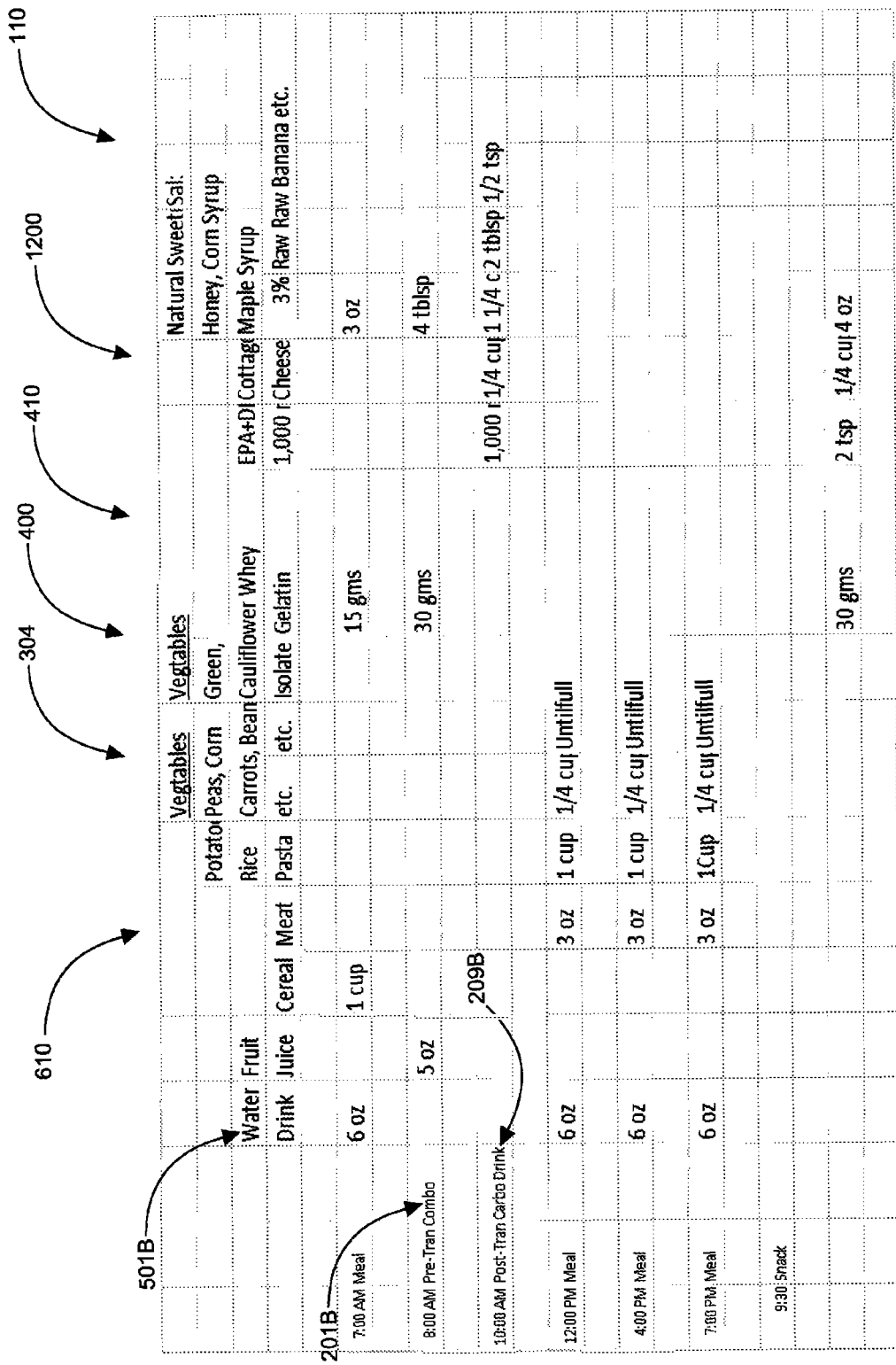
FIG. 12 illustrates an exemplary food schedule chart for use with the trainer-specified meal plan for the method of training athletes using ph balancing according to an embodiment of the present invention of FIGS. 1, 2, and 4-5 and 9-11.

FIG. 12 illustrates an exemplary food schedule chart 1200 for use with trainer-specified meal plan 410 for method and system of training athletes using ph balancing 110 according to an embodiment of the present invention of FIGS. 1, 2, and 4-5 and 9-11. Exemplary food schedule chart 1200 shows and provides recording means for trainer-specified meal plan 410. This is useful to 'track' inputs to athlete and to monitor progress over time.

FIG. 13 is a pH to Range conversion chart 1300 for use with method of training athletes using ph balancing 110 according to an embodiment of the present invention of FIGS. 1-3 and 5. pH to Range conversion chart 1300 is used to convert raw pH testing 103, pH testing 106, pH testing 203 (pH for saliva) and pH testing 303 (pH for urine) that are converted to ranges giving corresponding letter grades (A-E), (hereby enabling pH balancing 120). It should be emphasized that the ideal pH testing 203 and pH testing 303 is 6.4 as discussed previously. Stool sample texture is also related, all in relation to desired energy output available. In this way the present invention looks to promote health and available energy using visual representations.

FIG. 14 illustrates an exemplary daily pH recording chart 1400 for use with method of training athletes using ph balancing 110 according to an embodiment of the present invention of FIGS. 1-3, 5 and 13. Exemplary daily pH recording chart 1400 may be used to track pH testing 203 and pH testing 303 of saliva and urine throughout the day. In this way pH testing 203 and pH testing 303 may be tracked over time durations to work towards ideal pH of 6.4.

FIG. 15 illustrates a chart showing calcium rates 1500 for variable pH ranges for use with method of training athletes using ph balancing 110 according to an embodiment of the present invention of FIGS. 1-3, 13, and 14. Chart showing calcium rates 1500 is used to show recommended supplements to be taken according to pH range obtained from FIG. 13. Supplements (hereby enabling ingesting supplements 204) may include Calcium Lactate; Calcium Carbonate; Calcium Hydroxide; B12; and Tums. The appropriate number of suggested capsules and times to take the capsules per day is also referenced for ease of use. These and other charts 610 are preferably included in kit 640, as shown and discussed in FIG. 6. Charts 610 provided are exemplary and may be modified to fit the particular application, sport and body-style desired by trainer and/or athlete.

FIG. 16 illustrates a chart showing vitamin calculations for pH values 1600 for use with method of training athletes using ph balancing 110 according to an embodiment of the present invention of FIGS. 1-3, 5, 6, 13-15. Vitamin calculations for pH values 1600 are compared against pH testing 203 and pH testing 303 of saliva and urine (respectively) and recommended vitamins and doses are disclosed. In this way method and system of training athletes using ph balancing 110 is disclosed and enabled for use to promote health and to maximize athletic efficiency and longevity.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A method for training at least one athlete using body chemistry optimizing comprising the ordered steps of:
   a) eating from said trainer-specified meal plan;
   b) body chemistry testing of saliva and urine of said at least one athlete;
   c) wherein said pH body chemistry testing comprises testing pH,using a refractometer to test BRIX to obtain a visual readout, and at least one of the following: sugar, salt, albumen, or urea, from at least one saliva sample from said at least one athlete;
d) wherein a first pH measurement of said body chemistry testing is taken from said at least one saliva sample and a second pH measurement is taken from at least one urine sample and are compared to a pH range conversion chart to determine actual body pH;
e) training according to said trainer-specified training plan;
f) body chemistry testing of said saliva and said urine of said at least one athlete;
g) wherein said pH body chemistry testing comprises testing pH and at least one of the following: sugar, salt, albumen, or urea, from at least one saliva sample from said at least one athlete;
h) ingesting said supplements;
i) wherein said supplements comprise Calcium lactate, Calcium Carbonate, Calcium Hydroxide, Calcium Glucanate, and Vitamin C and Vitamin D;
j) eating from said trainer-specified meal plan;
k) wherein said trainer-specified meal plan comprises at least one post-train combo drink comprising Folic Acid, Vitamin D, protein source, lemon water beverage and at least one calcium supplement;
l) body chemistry testing of saliva and urine of said at least one athlete;
m) wherein said pH body chemistry testing comprises testing pH, using a refractometer to test BRIX to obtain a visual readout, and at least one of the following: sugar, salt, albumen, or urea, from at least one saliva sample from said at least one athlete;
n) wherein a first pH measurement of said body chemistry testing is taken from at least one saliva sample and a second pH measurement is taken from at least one urine sample and are compared to a pH range conversion chart to determine actual body pH;
o) ingesting said supplements;
p) training according to said trainer-specified training plan;
q) eating from said trainer-specified meal plan;
r) wherein the specific order must consist of:
  i) first said eating from said trainer-specified meal plan;
  ii) second said body chemistry testing of saliva and urine of said at least one athlete;
  iii) wherein said body chemistry testing comprises testing pH, using a refractometer to test BRIX to obtain a visual readout, and at least one of the following: sugar, salt, albumen, or urea, from at least one saliva sample from said at least one athlete;
  iv) third said training according to a trainer-specified training plan;
  v) fourth said body chemistry testing of saliva and urine of said at least one athlete;
  vi) fifth ingesting said supplements;
  vii) sixth eating from said trainer-specified meal plan;
  viii) seventh training according to said trainer-specified training plan; and
  ix) eighth said body chemistry testing of saliva and urine of said at least one athlete;
  x) ninth ingesting said supplements;
  xi) tenth training according to said trainer-specified training plan; and
  xii) eleventh eating from said trainer-specified meal plan.

* * * * *